(12) United States Patent
Yu (10) Patent No.: US 7,999,070 B2
(45) Date of Patent: Aug. 16, 2011

(54) PROCESS FOR SCREENING OF A BINDING PEPTIDE SPECIFIC FOR SPECIFIC RNA AND RNA BINDING PEPTIDES THEREFROM

(75) Inventor: Jaehoon Yu, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 968 days.

(21) Appl. No.: 11/457,773

(22) Filed: Jul. 14, 2006

(65) Prior Publication Data

US 2008/0318797 A1    Dec. 25, 2008

(30) Foreign Application Priority Data

Aug. 31, 2005 (KR) .................. 10-2005-0080903

(51) Int. Cl.
*A61K 38/00* (2006.01)
*C07K 7/00* (2006.01)
*C40B 40/10* (2006.01)
*C40B 30/04* (2006.01)
*C12Q 1/68* (2006.01)
*G01N 33/53* (2006.01)

(52) U.S. Cl. .............. 530/326; 530/323; 506/9; 506/18; 435/6; 435/7.1

(58) Field of Classification Search .................. 530/326, 530/323; 506/9, 18; 435/6, 7.1
See application file for complete search history.

(56) References Cited

U.S. PATENT DOCUMENTS 6,660,843 B1 * 12/2003 Feige et al. ................ 530/391.7
6,943,001 B2 *  9/2005 Zhao et al. ................... 435/195

FOREIGN PATENT DOCUMENTS

WO    WO 2006/135045    * 12/2006

OTHER PUBLICATIONS

McGregor, 2008, Discovering and improving novel peptide therapeutics, Current Opinion in Pharmacology, 8: 616-619.*
Stolk et al., 2004, Increasing number of anti-HIV drugs but no definite cure, Pharm. World Sci., 26: 133-136.*
Cox et al., 1985, The Interaction of Calmodulin with Amphiphilic Peptides, The Journal of Biological Chemistry, 260(4): 2527-2534.*
Watanabe et al., 2005, Anomalous reflection of gold applicable for a practical protein-detecting chip platform, Molecular BioSystems, 1: 363-365.*
Lawton and Appella, "Nonionic Side Chains Modulate the Affinity and Specificity of Binding Between Functionalized Polyamines and Structured RNA," J. Am. Chem. Soc. 126: 12762-12763 (2004).
Das and Frankel, "Sequence and Structure Space of RNA-Binding Peptides," Biopolymers, 70: 80-85 (2003).
Tan and Frankel, "Structural Variety of Arginine-Rich RNA-Binding Peptides," Proc. Natl. Acad. Sci. USA, 92: 5282-5286 (1995).
Liu and Dreyfuss, "In Vivo and In Vitro Arginine Methylation of RNA-Binding Proteins," Molecular and Cellular Biology, 15(5): 2800-2808 (1995).

* cited by examiner

*Primary Examiner* — Amber D. Steele
(74) *Attorney, Agent, or Firm* — JHK Law; Joseph Hyosuk Kim (57) ABSTRACT

The present invention relates to a screening method for RNA specific binding peptide using alpha-helical peptides. The screening method for RNA specific binding peptide of the present invention using alpha-helical peptides enables the selection of a peptide having strong binding capacity to a specific RNA having particular morphology and nucleotide sequence and the investigation of functions of RNA using the selected peptides, and is very useful for the production of a new drug using synthetic peptide having more powerful and specific binding capacity to RNA than those of natural peptides.

10 Claims, 1 Drawing Sheet

Fig. 1

SEQUENCE LISTING

```
<160> NUMBER OF SEQ ID NOS: 47

<210> SEQ ID NO 1
<211> LENGTH: 16
<212> TYPE: PRT
<213> ORGANISM: Artificial Sequence
<220> FEATURE:
<223> OTHER INFORMATION: synthesized

<400> SEQUENCE: 1

Leu Lys Lys Leu Leu Lys Leu Leu Lys Lys Leu Leu Lys Leu Lys Gly
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 2 is dimethylated

<400> SEQUENCE: 2

Leu Lys Lys Leu Leu Lys Leu Leu Lys Lys Leu Leu Lys Leu Lys Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 3 is dimethylated

<400> SEQUENCE: 3

Leu Lys Lys Leu Leu Lys Leu Leu Lys Lys Leu Leu Lys Leu Lys Gly
1               5                   10                  15
```

```
<210> SEQ ID NO 4
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 6 is dimethylated

<400> SEQUENCE: 4

Leu Lys Lys Leu Leu Lys Leu Leu Lys Lys Leu Leu Lys Leu Lys Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 9 is dimethylated

<400> SEQUENCE: 5

Leu Lys Lys Leu Leu Lys Leu Leu Lys Lys Leu Leu Lys Leu Lys Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 10 is dimethylated

<400> SEQUENCE: 6

Leu Lys Lys Leu Leu Lys Leu Leu Lys Lys Leu Leu Lys Leu Lys Gly
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 13 is dimethylated

<400> SEQUENCE: 7

Leu Lys Lys Leu Leu Lys Leu Leu Lys Lys Leu Leu Lys Leu Lys Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Sequence is synthesized- Lysine amino acid at
      position 15 is dimethylated

<400> SEQUENCE: 8

Leu Lys Lys Leu Leu Lys Leu Leu Lys Lys Leu Leu Lys Leu Lys Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 3 are dimethylated

<400> SEQUENCE: 9
```

Leu Lys Lys Leu Leu Lys Leu Leu Lys Lys Leu Leu Lys Leu Lys Gly
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 6 are dimethylated

<400> SEQUENCE: 10

Leu Lys Lys Leu Leu Lys Leu Leu Lys Lys Leu Leu Lys Leu Lys Gly
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 9 are dimethylated

<400> SEQUENCE: 11

Leu Lys Lys Leu Leu Lys Leu Leu Lys Lys Leu Leu Lys Leu Lys Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 10 are dimethylated

<400> SEQUENCE: 12

Leu Lys Lys Leu Leu Lys Leu Leu Lys Lys Leu Leu Lys Leu Lys Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 13 are dimethylated

<400> SEQUENCE: 13

Leu Lys Lys Leu Leu Lys Leu Leu Lys Lys Leu Leu Lys Leu Lys Gly
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2 and 15 are dimethylated

<400> SEQUENCE: 14

Leu Lys Lys Leu Leu Lys Leu Leu Lys Lys Leu Leu Lys Leu Lys Gly
1               5                   10                  15

<210> SEQ ID NO 15
<211> LENGTH: 16
<212> TYPE: PRT
<213> ORGANISM: Artificial Sequence
<220> FEATURE:

<223> OTHER INFORMATION: Sequence is synthesized- Lysine amino acids at
      positions 3 and 6 are dimethylated

<400> SEQUENCE: 15

Leu Lys Lys Leu Leu Lys Leu Leu Lys Lys Leu Leu Lys Leu Lys Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 3 and 9 are dimethylated

<400> SEQUENCE: 16

Leu Lys Lys Leu Leu Lys Leu Leu Lys Lys Leu Leu Lys Leu Lys Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 3 and 10 are dimethylated

<400> SEQUENCE: 17

Leu Lys Lys Leu Leu Lys Leu Leu Lys Lys Leu Leu Lys Leu Lys Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 3 and 13 are dimethylated

<400> SEQUENCE: 18

Leu Lys Lys Leu Leu Lys Leu Leu Lys Lys Leu Leu Lys Leu Lys Gly
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 3 and 15 are dimethylated

<400> SEQUENCE: 19

Leu Lys Lys Leu Leu Lys Leu Leu Lys Lys Leu Leu Lys Leu Lys Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6 and 9 are dimethylated

<400> SEQUENCE: 20

Leu Lys Lys Leu Leu Lys Leu Leu Lys Lys Leu Leu Lys Leu Lys Gly
1               5                   10                  15

<210> SEQ ID NO 21

-continued

```
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6 and 10 are dimethylated

<400> SEQUENCE: 21

Leu Lys Lys Leu Leu Lys Leu Leu Lys Lys Leu Leu Lys Leu Lys Gly
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6 and 13 are dimethylated

<400> SEQUENCE: 22

Leu Lys Lys Leu Leu Lys Leu Leu Lys Lys Leu Leu Lys Leu Lys Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6 and 15 are dimethylated

<400> SEQUENCE: 23

Leu Lys Lys Leu Leu Lys Leu Leu Lys Lys Leu Leu Lys Leu Lys Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 9 and 10 are dimethylated

<400> SEQUENCE: 24

Leu Lys Lys Leu Leu Lys Leu Leu Lys Lys Leu Leu Lys Leu Lys Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 9 and 13 are dimethylated

<400> SEQUENCE: 25

Leu Lys Lys Leu Leu Lys Leu Leu Lys Lys Leu Leu Lys Leu Lys Gly
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 9 and 15 are dimethylated

<400> SEQUENCE: 26

Leu Lys Lys Leu Leu Lys Leu Leu Lys Lys Leu Leu Lys Leu Lys Gly
```

```
1               5                  10                 15
```

<210> SEQ ID NO 27
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 10 and 13 are dimethylated

<400> SEQUENCE: 27

```
Leu Lys Lys Leu Leu Lys Leu Leu Lys Lys Leu Leu Lys Leu Lys Gly
1               5                  10                 15
```

<210> SEQ ID NO 28
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 10 and 15 are dimethylated

<400> SEQUENCE: 28

```
Leu Lys Lys Leu Leu Lys Leu Leu Lys Lys Leu Leu Lys Leu Lys Gly
1               5                  10                 15
```

<210> SEQ ID NO 29
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 13 and 15 are dimethylated

<400> SEQUENCE: 29

```
Leu Lys Lys Leu Leu Lys Leu Leu Lys Lys Leu Leu Lys Leu Lys Gly
1               5                  10                 15
```

<210> SEQ ID NO 30
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6 and 9 are dimethylated

<400> SEQUENCE: 30

```
Leu Lys Lys Leu Leu Lys Leu Leu Lys Lys Leu Leu Lys Leu Lys Gly
1               5                  10                 15
```

<210> SEQ ID NO 31
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6 and 13 are dimethylated

<400> SEQUENCE: 31

```
Leu Lys Lys Leu Leu Lys Leu Leu Lys Lys Leu Leu Lys Leu Lys Gly
1               5                  10                 15
```

<210> SEQ ID NO 32
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6 and 15 are dimethylated -continued

<400> SEQUENCE: 32

Leu Lys Lys Leu Leu Lys Leu Leu Lys Lys Leu Leu Lys Leu Lys Gly
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 9 and 13 are dimethylated

<400> SEQUENCE: 33

Leu Lys Lys Leu Leu Lys Leu Leu Lys Lys Leu Leu Lys Leu Lys Gly
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 9 and 15 are dimethylated

<400> SEQUENCE: 34

Leu Lys Lys Leu Leu Lys Leu Leu Lys Lys Leu Leu Lys Leu Lys Gly
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 13 and 15 are dimethylated

<400> SEQUENCE: 35

Leu Lys Lys Leu Leu Lys Leu Leu Lys Lys Leu Leu Lys Leu Lys Gly
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6, 10 and 13 are dimethylated

<400> SEQUENCE: 36

Leu Lys Lys Leu Leu Lys Leu Leu Lys Lys Leu Leu Lys Leu Lys Gly
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6, 10 and 15 are dimethylated

<400> SEQUENCE: 37

Leu Lys Lys Leu Leu Lys Leu Leu Lys Lys Leu Leu Lys Leu Lys Gly
1               5                   10                  15

<210> SEQ ID NO 38
<211> LENGTH: 16
<212> TYPE: PRT

```
<213> ORGANISM: Artificial Sequence
<220> FEATURE:
<223> OTHER INFORMATION: Sequence is synthesized- Lysine amino acids at
      positions 6, 13 and 15 are dimethylated

<400> SEQUENCE: 38

Leu Lys Lys Leu Leu Lys Leu Leu Lys Lys Leu Leu Lys Leu Lys Gly
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 9, 13 and 15 are dimethylated

<400> SEQUENCE: 39

Leu Lys Lys Leu Leu Lys Leu Leu Lys Lys Leu Leu Lys Leu Lys Gly
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6, 10 and 13 are dimethylated

<400> SEQUENCE: 40

Leu Lys Lys Leu Leu Lys Leu Leu Lys Lys Leu Leu Lys Leu Lys Gly
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 10, 13 and 15 are dimethylated

<400> SEQUENCE: 41

Leu Lys Lys Leu Leu Lys Leu Leu Lys Lys Leu Leu Lys Leu Lys Gly
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6, 13 and 15 are dimethylated

<400> SEQUENCE: 42

Leu Lys Lys Leu Leu Lys Leu Leu Lys Lys Leu Leu Lys Leu Lys Gly
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6, 9 and 15 are dimethylated

<400> SEQUENCE: 43

Leu Lys Lys Leu Leu Lys Leu Leu Lys Lys Leu Leu Lys Leu Lys Gly
1               5                   10                  15
```

```
<210> SEQ ID NO 44
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 6, 9, 13 and 15 are dimethylated

<400> SEQUENCE: 44

Leu Lys Lys Leu Leu Lys Leu Leu Lys Lys Leu Leu Lys Leu Lys Gly
1               5                  10                  15

<210> SEQ ID NO 45
<211> LENGTH: 16
<212> TYPE: PRT
<213> ORGANISM: Artificial Sequence
<220> FEATURE:
<223> OTHER INFORMATION: Sequence is synthesized- Lysine amino acids at
      positions 2, 6, 9, 13 and 15 are dimethylated

<400> SEQUENCE: 45

Leu Lys Lys Leu Leu Lys Leu Leu Lys Lys Leu Leu Lys Leu Lys Gly
1               5                  10                  15

<210> SEQ ID NO 46
<211> LENGTH: 50
<212> TYPE: DNA
<213> ORGANISM: Artificial Sequence
<220> FEATURE:
<223> OTHER INFORMATION: Sequence is synthesized- RRE DNA sense strand

<400> SEQUENCE: 46
ccgtaatacg actcactata ggtgggcgca gcttcggctg acggtacacc              50

<210> SEQ ID NO 47
<211> LENGTH: 50
<212> TYPE: DNA
<213> ORGANISM: Artificial Sequence
<220> FEATURE:
<223> OTHER INFORMATION: Sequence is synthesized- RRE DNA antisense
      strand

<400> SEQUENCE: 47
ggtgtaccgt cagccgaagc tgcgcccacc tatagtgagt cgtattacgg              50
```

PROCESS FOR SCREENING OF A BINDING PEPTIDE SPECIFIC FOR SPECIFIC RNA AND RNA BINDING PEPTIDES THEREFROM

TECHNICAL FIELD

The present invention relates to a screening method for a peptide binding specifically to RRE RNA, one of HIV-1 targets, using alpha-helical peptide.

BACKGROUND ART

According to the completion of the genome project for both human and various target animals and plants and the development of bioinformatics, mRNA has been proved to act as a messenger transmitting genetic information of DNA to a protein and at the same time to regulate the gene expression.

Since the beginning of year 2000, micro-RNA (miRNA) or its precursor pre-miRNA has been proved to regulate 10-20% of gene functions. In prokaryotes, some parts of mRNA are directly bound with a metabolite, suggesting that it has ribo-switch that regulates the functions of metabolite related protein. It has been also confirmed that the secondary structure of untranslating region of mRNA of higher animals regulates mRNA stability and translation efficiency.

The numbers of such RNA that has regulatory function are considerable. The structure of the RNA is composed of a series of hairpin structures in which stems and loops (basic motif) are arranged serially. It is also presumed that pharmacophore of natural miRNA or biologically significant mRNA might be the specific stem-loop (hairpin) structure, which is less than 30 nt, considering the size of binding region of ribo-switch to a compound.

Although every mRNA has been proved to have secondary structure, the confirmed mRNA hairpin structures are very few, which are only exemplified by Rev Response Element (RRE) of HIV-1, trans-activation response element (TAR) of HIV-1, Thymidylate Synthase mRNA of various tumor cells and Ion Responsive Element (IRE) involved in homeostasis of iron ion and dementia, which is attributed to the lack of biological methods, the lack of information on RNA-binding protein and insufficient information on hairpin structure, etc. However, RNA targets having the hairpin structure are highly expected to be major biological targets and so great effort has to be made to find out ligands against such pouring RNA targets.

Polyamines having several amine groups have been produced by imitating the conventional RNA pro-binding aminoglycoside compound, which have also been confirmed to be bound with RNA targets very well (Lawton et al., J. Am. Chem. Soc., 126: 12762-12763, 2004). Successively, morphology of a protein was observed according to the methylation of an amino acid containing amine group existing in natural RNA binding protein (Das and Frankel, Biopolymers, 70: 80-85, 2003). From the investigation of natural RNA binding proteins and binding peptides was confirmed that lysine or arginine which contains a large number of amine groups was included in the peptides and such proteins or peptides were already methylated considerably (Tan and Fankel, Proc Natl Acad Sci USA. 92, 5282-5286, 1995). It was additionally confirmed that RNA binding capacity was increased as methylation of arginine of RNA binding protein proceeded (Liu and Dreyfuss, Mol Cell Biol. 15, 2800-2808, 1995).

There have been a great numbers of reports on RNA binding capacity of a peptide containing amine group or RNA binding capacity depending on the methylation of amine group and natural RNA binding peptides and methylation of them. However, there was no report yet on synthesized RNA binding peptide or specific RNA binding capacity of a methylated peptide. Therefore, to obtain a peptide specifically binding to RNA, the present inventors prepared a peptide composed of 15 amino acids containing 7 alpha-helical lysines. In the meantime, to ensure the diversity of such peptides, a library was constructed by using the combination of methylated lysines. Then, the present inventors completed this invention by selecting peptides showing the strongest binding capacity to RRE-RNA of HIV-1 from those synthesized from the library. The peptide of the present invention thus has not only strong but also specific RRE RNA binding capacity, so that it can be used as a therapeutic agent for AIDS.

DISCLOSURE

Technical Problem

It is an object of the present invention to provide a screening method for RNA specific binding peptide using artificially synthesized alpha-helical peptide.

Technical Solution

The present invention provides an alpha-helical peptide library containing synthesized alpha-helical peptides having plural basic amino acids or modified alpha-helical peptides in which at least one of those basic amino acids is methylated. The basic amino acids are exemplified by lysine, arginine, histidine or 5-hydroxy lysine but not always limited thereto. The synthesized alpha-helical peptide is characterized by being composed of amino acids having from at least 14 to more than 150 amino acids having hydrophobicity and amino acids having amine group, to have stable secondary structure which is helical structure. The synthesized alpha-helical peptide is also characterized by that the basic amino acids are located at every third or forth amino acid site of the synthesized alpha-helical peptide sequence in order to arrange the basic amino acids for standing in a line.

The present invention provides a library of alpha-helical peptide represented by SEQ. ID. No 1.

The present invention also provides an alpha-helical peptide library characteristically including one or more alpha-helical peptides represented by SEQ. ID. No 1-45.

The present invention further provides a screening method for RNA specific binding peptide using the alpha-helical peptide library.

The present invention also provides a screening method for RNA specific binding peptide using alpha-helical peptide library comprising the following steps:

(i) constructing alpha-helical peptide library and purifying the peptides;

(ii) synthesizing a specific binding RNA;

(iii) calculating the binding strength of RNA and peptide by measuring fluorescence anisotropy of the mixture of the peptide, the specific binding RNA and probe molecule with fluorescence spectrophotometer; and (iv) selecting of a peptide showing strong specific RNA binding capacity.

In the present invention, RRE RNA of HIV-1 was selected as the specific RNA but the selection is not always limited thereto. Every tag-labeled compound that is able to be detected by fluorescence spectrophotometer and be bound to RNA by competing over a RNA binding peptide is used as a probe molecule, but not always limited thereto. In particular, however, CRP (5-carboxytetramethylrhodamine labeled paromomycin) is more preferred.

The present invention provides a specific RNA specific binding peptide screened by the method of invention that is a screening method of RNA specific binding peptide using alpha-helical peptide library.

The present invention also provides RRE RNA binding peptides represented by SEQ. ID. No 1, No 3, No 7, No 16, No 18, No 25 and No 33, detected by the screening method of RNA specific binding peptide using alpha-helical peptide library or analogues of those peptides. Those peptide analogues are characterized by that basic amino acid is replaced with arginine, histidine or 5-hydroxy lysine, or hydrophobic amino acid except basic amino acid is replaced with another hydrophobic amino acid, but they have the equal functions to the peptides themselves.

The present invention also provides a RNA activity inhibitor containing specific RNA specific binding peptide as an effective ingredient which is detected by the screening method for RNA specific binding peptide using alpha-helical peptide library.

The present invention further provides a therapeutic agent for AIDS containing RRE RNA binding peptide as an effective ingredient which is represented by SEQ. ID. No 1, No 3, No 7, No 16, No 18, No 25 or No 33 and detected by the screening method for RNA specific binding peptide using alpha-helical peptide library.

Many compounds have been used as a drug by distinguishing different structures of proteins, suggesting that compounds surpass proteins in diversity. Less diverse structures of RNA than those of proteins can be easily distinguished by various compounds theoretically.

The most representative RNA binding peptide is aminoglycoside, in the structure of which 3~4 hexagon sugars are linked and 6~7 amine functional groups are included as well. Although aminoglycoside is a natural RNA binding material, its specific binding capacity is not very good. Thus, to develop a new drug targeting RNA, a RNA binding peptide with excellent specificity is required.

Natural RNA binding peptides have been studied so far and most of them are proved to be alpha-helical and contain a large number of arginines/lysines having amine group.

Based on the above founding, a synthetic RNA binding peptide can be designed to contain numbers of lysines. To have a stable secondary structure, a peptide needs to be composed of from at least 14 to more than 150 amino acids, ensuring RNA specific binding capacity. To line up amine groups in one side of a helical peptide, a pair of lysines have to be positioned every second or every third location of a peptide sequence (LKKLLKLLKKLLKLKG) (SEQ. ID. No. 1). However, the sequence available for the present invention is not limited thereto, and any other sequence that is formed with alpha-helical and is able to construct helix even with the replacement of amino acids except basic amino acids with other hydrophobic amino acids can be also used.

Nevertheless, diversity of useful peptides is still too unsatisfying if RNA specific binding peptide is produced only by using lysine and arginine. Thus, various kinds of peptides should be firstly prepared and among them the most promising candidate for specific RNA specific binding peptide has to be selected by RNA screening method of the invention to provide RNA specific ligand.

Considering the reports saying that methylation of basic amino acid such as lysine or arginine promotes RNA binding capacity of a peptide, a peptide having pre-methylated lysine/arginine seems to have enough RNA specific binding capacity. Instead of using lysine for the production of a synthetic peptide, locating methylated lysine at amine region at the end of lysine can provided improved diversity. In addition to the three possible methylation patterns (mono, di and tri), the possibility of having unmethylated lysine each in 9 lysines should be counted, so that a peptide library with diversity of $4^9=262,000$ is constructed. By using this peptide library with such diversity, a specific RNA specific peptide is selected to prepare specific RNA ligand.

In preferred embodiments of the present invention, in stead of constructing a peptide library having 262,000 peptides using lysine and methylated lysine (mono-, di- or tri-methylated lysine), the present inventors constructed a partial peptide library having $2^9=512$ by locating lysine and dimethylated lysine in the sites of 9 lysines by using lysine and two methyl groups binding lysine and screened the library on RRE RNA of HIV-1 to select a peptide having the strongest RNA binding capacity.

In the embodiments of the invention, various peptides could be prepared by using methylated lysines, and those different peptides showed different specificity, which was a good asset to finding of a RRE RNA specific binding peptide. The binding capacity is lower than the level of nano molar but is 1,000 times increased, compared with that of well-known neomycin. Considering that the binding capacity of neomycin is comparatively high, those peptides seemed to have great possibility of being a potential new drug.

The detailed investigation on the specificity of peptide 16 (SEQ. ID. No 16) was not performed in the present invention, however the binding capacity to TAR RNA and tRNA, general peptides having stem-loop, was tested by fluorescence anisotropy. As a result, the binding capacity was hundreds and tens μM, which was not good at all, so the binding capacity to RRE RNA of peptide 16 (SEQ. ID. No 16) was considered to be significantly specific.

Therefore, the present invention also provides a preparation method for RNA specific ligand by constructing a peptide library using methylated lysine and then selecting a peptide showing strong binding capacity to a target RNA.

MODE FOR INVENTION

Figure 1:
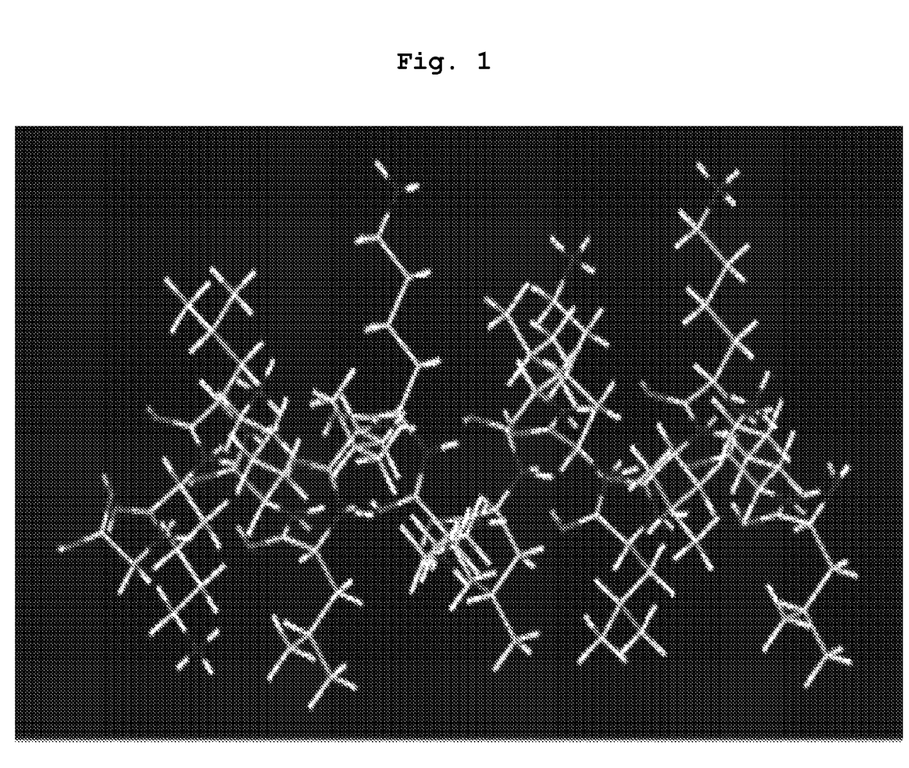
FIG. 1 is a picture showing the morphology of a peptide having alpha-helical structure.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of Peptide Library

Fmoc-lysine, Fmoc-dimethylated lysine and leucine were all purchased from Novagen (USA). All peptides were used to synthesize a peptide having the amino acid sequence 'LKKLLKLLKKLLKLKG (SEQ. ID. No 1)' by the scale of 0.5 μM. To synthesize a solid phase peptide, 100 mg (0.064 mmol) of Rink Amide MBHA resin (Novabiochem, Germany) was put in a vessel, to which 1 ml of methylene chloride was added. The mixture was inflated for 5 minutes. 1 ml of DMF (dimethylformamide) was added and then the mixture was inflated again for 5 minutes. Deprotection of the resin was performed with 1 ml of 20% piperidine (in DMF) for 5 minutes (repeated three times), followed by washing with 1 ml of DMF five times Amino acid in which 6 equivalents of Fmoc are deprotected, 6 equivalents (198 mg) of PyBop Rbenzotriazol-1-yloxy)tripyrrolidinophosphonium hexafluorophosphate] and 12 equivalents (133 µl) of DIPEA (diisopropylethylamine) were mixed, which was stirred for 2 hours. Upon completion of the reaction, the reaction solution was washed with 1 ml of DMF three times. Kaiser test was performed to confirm weather or not amide bonding was completed, that is 5 g of ninhydrin in 100 ml of ethanol, 80 g of liquid phenol and potassium cyanide in 20 ml of ethanol and 2 ml of 0.001 M of aqueous solution were added to 98 ml of pyridine, which was dropped on each sample by three drops. The samples were heated at 100° C. for 5 minutes. Then the sample without showing any color was regarded as reaction was completed therein. Once amide bonding was completed, which was considered as one cycle, the cycle was repeated 16 times to synthesize 16-mer peptide. After finishing the last coupling, the resin was washed three times respectively with 1 ml of DMF and 1 ml of methanol. Then, the resin was dried under vacuum condition. 200 mg of resin containing the peptide synthesized by the solid phase peptide synthesizing method above was put in 5 ml of cleavage solution [2.5% TIS (triisopropylsilane), 2.5% water, 95% TFA (trifluoroacetic acid)], followed by stirring for 2 hours. The resin was filtered. The excessive TFA was eliminated by using nitrogen from the filtered solution. 50 ml of n-hexane:diethyl ether=1:1 solution, which was cooled down at 0° C. in advance, was added to the reaction solution to extract a peptide synthesized. The extracted peptide was dissolved in dimethyl sulfoxide and purified by HPLC using C18 column. As a HPLC solvent, water containing 0.1% TFA and acetonitrile were used.

Example 2

Purification of Peptide

Crude peptide was dissolved in dimethyl sulfoxide at the concentration of 10 mg/ml, which was injected in HPLC by 100 µl at a time. The composition of solvent was changed from 10% acetonitrile to 45% acetonitrile for 40 minutes to purify the peptide. At that time, fluid velocity was 4 ml/min, and wave length was 220 nm. Peptide was recovered at the time point of 20-30 minutes. The recovered peptide solution was decompressed to vaporize acetonitrile, followed by freeze-drying. The molecular weight of the synthesized peptide was measured by MULDI-TOF mass spectrometry and the peptide was resultantly identified.

<2-1> Synthesis of Peptides 1~45 and their Molecular Weights

LKKLLKLLKKLLKLKG (peptide 1: SEQ. ID. No 1) was synthesized in analogy to the procedure described above. Mass (M+H); 1877.5 (calcd.), 1877.2 (obsvd.).

LK*KLLKLLKKLLKLKG (peptide 2: SEQ. ID. No 2) was synthesized in analogy to the procedure described above. Mass (M+H); 1905.6 (calcd.), 1905.6 (obsvd.) K* is dimethylated lysine.

LKK*LLKLLKKLLKLKG (peptide 3: SEQ. ID. No 3) was synthesized in analogy to the procedure described above. Mass (M+H); 1905.6 (calcd.), 1905.3 (obsvd.) K* is dimethylated lysine.

LKKLLK*LLKKLLKLKG (peptide 4: SEQ. ID. No 4) was synthesized in analogy to the procedure described above. Mass (M+H); 1905.6 (calcd.), 1905.4 (obsvd.) K* is dimethylated lysine.

LKKLLKLLK*KLLKLKG (peptide 5: SEQ. ID. No 5) was synthesized in analogy to the procedure described above. Mass (M+H); 1905.6 (calcd.), 1905.4 (obsvd.) K* is dimethylated lysine.

LKKLLKLLKK*LLKLKG (peptide 6: SEQ. ID. No 6) was synthesized in analogy to the procedure described above. Mass (M+H); 1905.6 (calcd.), 1905.5 (obsvd.) K* is dimethylated lysine.

LKKLLKLLKKLLK*LKG (peptide 7: SEQ. ID. No 7) was synthesized in analogy to the procedure described above. Mass (M+H); 1905.6 (calcd.), 1905.5 (obsvd.) K* is dimethylated lysine.

LKKLLKLLKKLLKLK*G (peptide 8: SEQ. ID. No 8) was synthesized in analogy to the procedure described above. Mass (M+H); 1905.6 (calcd.), 1905.3 (obsvd.) K* is dimethylated lysine.

LK*K*LLKLLKKLLKLKG (peptide 9: SEQ. ID. No 9) was synthesized in analogy to the procedure described above. Mass (M+H); 1933.6 (calcd.), 1933.1 (obsvd.) K* is dimethylated lysine.

LK*KLLK*LLKKLLKLKG (peptide 10: SEQ. ID. No 10) was synthesized in analogy to the procedure described above. Mass (M+H); 1933.6 (calcd.), 1932.1 (obsvd.) K* is dimethylated lysine.

LK*KLLKLLK*LLKLKG (peptide 11: SEQ. ID. No 11) was synthesized in analogy to the procedure described above. Mass (M+H); 1933.6 (calcd.), 1932.1 (obsvd.) K* is dimethylated lysine.

LK*KLLKLLKK*LLKLKG (peptide 12: SEQ. ID. No 12) was synthesized in analogy to the procedure described above. Mass (M+H); 1933.6 (calcd.), 1932.1 (obsvd.) K* is dimethylated lysine.

LK*KLLKLLKKLLK*LKG (peptide 13: SEQ. ID. No 13) was synthesized in analogy to the procedure described above. Mass (M+H); 1933.6 (calcd.), 1932.1 (obsvd.) K* is dimethylated lysine.

LK*KLLKLLKKLLKLK*G (peptide 14: SEQ. ID. No 14) was synthesized in analogy to the procedure described above. Mass (M+H); 1933.6 (calcd.), 1933.5 (obsvd.) K* is dimethylated lysine.

LKK*LLK*LLKKLLKLKG (peptide 15: SEQ. ID. No 15) was synthesized in analogy to the procedure described above. Mass (M+H); 1933.6 (calcd.), 1933.4 (obsvd.) K* is dimethylated lysine.

LKK*LLKLLK*KLLKLKG (peptide 16: SEQ. ID. No 16) was synthesized in analogy to the procedure described above. Mass (M+H); 1933.6 (calcd.), 1933.4 (obsvd.) K* is dimethylated lysine.

LKK*LLKLLKK*LLKLKG (peptide 17: SEQ. ID. No 17) was synthesized in analogy to the procedure described above. Mass (M+H); 1933.6 (calcd.), 1933.2 (obsvd.) K* is dimethylated lysine.

LKK*LLKLLKKLLK*LKG (peptide 18: SEQ. ID. No 18) was synthesized in analogy to the procedure described above. Mass (M+H); 1933.6 (calcd.), 1933.3 (obsvd.) K* is dimethylated lysine.

LKK*LLKLLKKLLKLK*G (peptide 19: SEQ. ID. No 19) was synthesized in analogy to the procedure described above. Mass (M+H); 1933.6 (calcd.), 1933.7 (obsvd.) K* is dimethylated lysine.

LKKLLK*LLK*KLLKLKG (peptide 20: SEQ. ID. No 20) was synthesized in analogy to the procedure described above. Mass (M+H); 1933.6 (calcd.), 1933.8 (obsvd.) K* is dimethylated lysine.

LKKLLK*LLKK*LLKLKG (peptide 21: SEQ. ID. No 21) was synthesized in analogy to the procedure described above. Mass (M+H); 1933.6 (calcd.), 1933.7 (obsvd.) K* is dimethylated lysine.

LKKLLK*LLKKLLK*LKG (peptide 22: SEQ. ID. No 22) was synthesized in analogy to the procedure described above. Mass (M+H); 1933.6 (calcd.), 1933.5 (obsvd.) K* is dimethylated lysine.

LKKLLK*LLKKLLKLK*G (peptide 23: SEQ. ID. No 23) was synthesized in analogy to the procedure described above. Mass (M+H); 1933.6 (calcd.), 1933.5 (obsvd.) K* is dimethylated lysine.

LKKLLKLLK*K*LLKLKG (peptide 24: SEQ. ID. No 24) was synthesized in analogy to the procedure described above. Mass (M+H); 1933.6 (calcd.), 1933.3 (obsvd.) K* is dimethylated lysine.

LKKLLKLLK*KLLK*LKG (peptide 25: SEQ. ID. No 25) was synthesized in analogy to the procedure described above. Mass (M+H); 1933.6 (calcd.), 1933.6 (obsvd.) K* is dimethylated lysine.

LKKLLKLLK*KLLKLK*G (peptide 26: SEQ. ID. No 26) was synthesized in analogy to the procedure described above. Mass (M+H); 1933.6 (calcd.), 1932.6 (obsvd.) K* is dimethylated lysine.

LKKLLKLLKK*LLK*LKG (peptide 27: SEQ. ID. No 27) was synthesized in analogy to the procedure described above. Mass (M+H); 1933.6 (calcd.), 1933.6 (obsvd.) K* is dimethylated lysine.

LKKLLKLLKK*LLKLK*G (peptide 28: SEQ. ID. No 28) was synthesized in analogy to the procedure described above. Mass (M+H); 1933.6 (calcd.), 1934.1 (obsvd.) K* is dimethylated lysine.

LKKLLKLLKKLLK*LK*G (peptide 29: SEQ. ID. No 29) was synthesized in analogy to the procedure described above. Mass (M+H); 1933.6 (calcd.), 1933.5 (obsvd.) K* is dimethylated lysine.

LK*KLLK*LLK*KLLKLKG (peptide 30: SEQ. ID. No 30) was synthesized in analogy to the procedure described above. Mass (M+H); 1961.7 (calcd.), 1961.4 (obsvd.) K* is dimethylated lysine.

LK*KLLK*LLKKLLK*LKG (peptide 31: SEQ. ID. No 31) was synthesized in analogy to the procedure described above. Mass (M+H); 1961.7 (calcd.), 1961.5 (obsvd.) K* is dimethylated lysine.

LK*KLLK*LLKKLLKLK*G (peptide 32: SEQ. ID. No 32) was synthesized in analogy to the procedure described above. Mass (M+H); 1961.7 (calcd.), 1961.4 (obsvd.) K* is dimethylated lysine.

LK*KLLKLLK*KLLK*LKG (peptide 33: SEQ. ID. No 33) was synthesized in analogy to the procedure described above. Mass (M+H); 1961.7 (calcd.), 1961.4 (obsvd.) K* is dimethylated lysine.

LK*KLLKLLK*KLLKLK*G (peptide 34: SEQ. ID. No 34) was synthesized in analogy to the procedure described above. Mass (M+H); 1961.7 (calcd.), 1961.2 (obsvd.) K* is dimethylated lysine.

LK*KLLKLLKKLLK*LK*G (peptide 35: SEQ. ID. No 35) was synthesized in analogy to the procedure described above. Mass (M+H); 1961.7 (calcd.), 1961.6 (obsvd.) K* is dimethylated lysine.

LKKLLK*LLKK*LLK*LKG (peptide 36: SEQ. ID. No 36) was synthesized in analogy to the procedure described above. Mass (M+H); 1961.7 (calcd.), 1961.8 (obsvd.) K* is dimethylated lysine.

LKKLLK*LLKK*LLKLK*G (peptide 37: SEQ. ID. No 37) was synthesized in analogy to the procedure described above. Mass (M+H); 1961.7 (calcd.), 1961.5 (obsvd.) K* is dimethylated lysine.

LKKLLK*LLKKLLK*LK*G (peptide 38: SEQ. ID. No 38) was synthesized in analogy to the procedure described above. Mass (M+H); 1961.7 (calcd.), 1961.7 (obsvd.) K* is dimethylated lysine.

LKKLLKLLK*KLLK*LK*G (peptide 39: SEQ. ID. No 39) was synthesized in analogy to the procedure described above. Mass (M+H); 1961.7 (calcd.), 1961.5 (obsvd.) K* is dimethylated lysine.

LK*KLLK*LLKK*LLK*LKG (peptide 40: SEQ. ID. No 40) was synthesized in analogy to the procedure described above. Mass (M+H); 1989.8 (calcd.), 1989.6 (obsvd.) K* is dimethylated lysine.

LK*KLLK*LLKK*LLK*LK*G (peptide 41: SEQ. ID. No 41) was synthesized in analogy to the procedure described above. Mass (M+H); 1989.8 (calcd.), 1989.1 (obsvd.) K* is dimethylated lysine.

LK*KLLK*LLKKLLK*LK*G (peptide 42: SEQ. ID. No 42) was synthesized in analogy to the procedure described above. Mass (M+H); 1989.8 (calcd.), 1989.0 (obsvd.) K* is dimethylated lysine.

LK*KLLK*LLK*KLLKLK*G (peptide 43: SEQ. ID. No 43) was synthesized in analogy to the procedure described above. Mass (M+H); 1989.8 (calcd.), 1989.9 (obsvd.) K* is dimethylated lysine.

LKKLLK*LLK*KLLK*LK*G (peptide 44: SEQ. ID. No 44) was synthesized in analogy to the procedure described above. Mass (M+H); 1989.8 (calcd.), 1989.6 (obsvd.) K* is dimethylated lysine.

LK*KLLK*LLK*KLLK*LK*G (peptide 45: SEQ. ID. No 45) was synthesized in analogy to the procedure described above. Mass (M+H); 2017.9 (calcd.), 2017.9 (obsvd.) K* is dimethylated lysine.

Example 3

Preparation of RRE RNA of HIV-1

To transform single-stranded RRE DNA (sense: 5'-CCg TAA TAC gAC TCA CTA TAg gTg ggC gCA gCT TCg gCT gAC ggT ACA CC-3' (SEQ. ID. No 46), antisense: 5'-ggT gTA CCg TCA gCC gAA gCT gCg CCC ACC TAT AgT gAg TCg TAT TAC gg-3' (SEQ. ID. No 47)) which T7 promoter was attached on into double-stranded DNA, 100 pmol of RRE sense DNA strand and 100 pmol of RRE antisense DNA strand were mixed, followed by reaction at 95° C. for 5 minutes. The reaction mixture was cooled down slowly at room temperature.

For transcription, 100 μmol of double-stranded RRE DNA, 20 μl of 5× buffer solution (200 mM Tris-Cl, (pH7.5), 10 mM spermidin, 30 mM MgCl$_2$, 25 mM NaCl), 10 μl of 100 mM DTT (dithiothreitol), 20 μl of 2.5 mM NTP (ribonucleoside triphosphate) mix and 5 μl of T7 RNA polymerase were mixed. The mixture was reacted at 37° C. for 4 hours, to which 1 μl of RQ1 RNase-free DNase (1 unit/μl) (PROMEGA, USA) was added, followed by reaction for one hour under the same condition as above. Protein was removed by adding the equal amount of phenol mixture (Phenol:Chloroform:Isoamyl alcohol=25:24:1), and precipitation was induced using ethanol at −70° C. for one hour. The precipitate was loaded on 15% denaturation PAGE gel containing 7 M urea, then exactly 30-mer size band was cut off and put in eppendorf tube containing 500 μl of elution buffer (0.5 M ammonium acetate, 1 mM EDTA, 0.2% SDS, pH 8.0), which stood at 37° C. for 4 hours. Only the solution was transferred into a new eppendorf tube, followed by phenol extraction by the same manner as described above. Aqueous solution layer containing RNA was precipitated by using ethanol, and then resultant RNA was quantified by UV.

Example 4

Measurement of Binding Capacity of Peptide to RRE RNA 100 ml of RRE RNA solution was prepared at the concentration of 10 mM, which stood at 65° C. for 10 minutes. Then, the solution was cooled down slowly at room temperature to induce folding. Peptide solution was prepared respectively at the concentration of 100 mM and 1.0 mM, and both of them were maintained at 0° C. 10 mm CRP (5-carboxytetramethylrhodamine labeled paromomycin) was prepared as a probe. Buffer solution was prepared by mixing 140 mM NaCl, 5 mM KCl, 1 mM MgCl$_2$ and 20 mM HEPES (N-2-Hydroxyethylpiperazine-N'-2-Ethanesulfonic Acid, pH 7.4). Fluorescence anisotropy was measured with AMINCO-Bowman Series Luminescence Spectrometer at 20° C. 10 nM CRP was added to 450 mL of buffer solution, to which RRE RNA was added in order to combine CRP with RNA. At that time, anisotropy was increased. Thereafter, peptide competitively binding to CRP was added and the changes of anisotropy were measured. The binding capacity to RRE RNA of the peptide was determined by the KaleidaGraph as follows;

$$[Peptide]=Kd(A\max-A)/[Kd(A-A0)+1]*[RNA]-Kd(A-A0)/(A\max-A)[CRP]0(A-A0)/(A\max-A0)$$

[Peptide] indicates the concentration of the peptide, [RNA] indicates the concentration of RNA and [CRP] indicates the concentration of CRP. A is the value of fluorescence anisotropy of a sample, Amax is the value of totally bound tracer and A0 is the value of totally free tracer.

The binding capacity of the identified peptide to RRE RNA (Kd) is as follows:

peptide 1, 0.0058 mM; peptide 2, 0.20 mM; peptide 3, 0.16 mM;

peptide 4, 0.28 mM; peptide 5, 0.34 mM; peptide 6, 0.16 mM;

peptide 7, 0.24 mM; peptide 8, 0.54 mM; peptide 9, 0.32 mM;

peptide 10, 0.16 mM; peptide 11, 0.16 mM; peptide 12, 0.16 mM;

peptide 13, 0.18 mM; peptide 14, 0.19 mM; peptide 15, 0.17 mM;

peptide 16, 0.00052 mM; peptide 17, 0.19 mM; peptide 18, 0.042 mM;

peptide 19, 0.19 mM; peptide 20, 0.23 mM; peptide 21, 0.29 mM;

peptide 22, 0.23 mM; peptide 23, 0.40 mM; peptide 24, 0.32 mM;

peptide 25, 0.039 mM; peptide 26, 0.23 mM; peptide 27, 0.32 mM;

peptide 28, 0.33 mM; peptide 29, 0.18 mM; peptide 30, 0.17 mM;

peptide 31, 0.19 mM; peptide 32, 0.23 mM; peptide 33, 0.044 mM;

peptide 34, 0.18 mM; peptide 35, 0.32 mM; peptide 36, 0.44 mM;

peptide 37, 0.20 mM; peptide 38, 0.23 mM; peptide 39, 0.16 mM;

peptide 40, 0.20 mM; peptide 41, 0.24 mM; peptide 42, 0.19 mM; and peptide 43, 0.40 mM; peptide 44, 0.20 mM; peptide 45, 0.17 mM.

From the above experiments, peptide 16 (SEQ. ID. No 16) that showed stronger binding capacity to RRE RNA than 1 nM was identified and several other peptides having similar binding capacity were also found.

Example 5

Measurement of Circular Dichroism (CD) of the Selected Peptide

CD was measured at 20° C. by using JASCO model J715 spectropolarimeter. Scanning of 190-260 nm wave length was performed three times with 1 nm of bandwidth, 0.5 nm of datapitch and 100 nm/min speed. The results of the scanning were averaged to obtain CD data. Background spectrum was measured to correct the basic spectrum, and CD signals were converted into mean residue ellipticity [Q]. The percentage of alpha-helix (fn) is calculated by the following formula.

$$[Q]=Qobs/\text{MRW}/(101c)]$$

MRW=mean residue weight (molecular weight is divided by the number of peptide bond), I=length of passway (cm), C=concentration (mg/mL).

$$fn=([Q]222-[Q]\text{coil})/([Q]\text{helix}-[Q]\text{coil})$$

[Q]helix=−40,000(1−2.5n)+100t

[Q]coil=640−45t

[Q]222=mean residue ellipticity (deg cm2 mol−1) at 222 nm, [Q]helix=ellipticity of authentic helical peptide, [Q]coil=ellipticity of authentic random coil peptide, n=number of amino acid, t=° C.

The degree and morphology of alpha-helices of 7 peptides having strong RNA binding capacity were investigated and the results were as follows. The number in a parenthesis suggests the comparison with Rev peptide (natural RRE RNA binding peptide).

peptide 1, 15 (2.2); peptide 7, 2.7 (0.40); peptide 3, 4.9 (0.72); peptide 25, 6.6 (1.0); peptide 18, 4.9 (0.71); peptide 16, 13 (2.0); peptide 33, 7.5 (1.1).

As confirmed in the above results, peptide 16 showed the next best alpha-helical structure percentage, following peptide 1, which indicates that the more alpha-helical structure, the stable the morphology of peptide, enabling RRE RNA specific binding. However, excessive methylation reduced the binding capacity, suggesting that recognition between methylated peptide of lysine and base of RNA is done in a specific way.

INDUSTRIAL APPLICABILITY

As explained hereinbefore, the present invention provides a screening method for RNA specific binding peptide using alpha-helical peptides, which enables the selection of a specific peptide having strong binding capacity to a specific RNA (RNA with specific morphology and nucleotide sequence) and is applicable for the investigation of functions of RNA particularly using the selected peptides and is very useful for the development of a new drug rather using synthetic peptide powerfully specifically binding to a target RNA than using a natural peptide.

[Sequence List Text]

The peptide sequence represented by SEQ. ID. No 1 is the sequence of alpha-helical peptide, The peptide sequence represented by SEQ. ID. No 2 is the sequence of alpha-helical peptide represented by SEQ. ID. No 1 in which the 2nd amino acid is replaced with dimethylated lysine, The peptide sequence represented by SEQ. ID. No 3 is the sequence of alpha-helical peptide represented by SEQ. ID. No 1 in which the 3rd amino acid is replaced with dimethylated lysine, The peptide sequence represented by SEQ. ID. No 4 is the sequence of alpha-helical peptide represented by SEQ. ID. No 1 in which the 6th amino acid is replaced with dimethylated lysine, The peptide sequence represented by SEQ. ID. No 5 is the sequence of alpha-helical peptide represented by SEQ. ID. No 1 in which the 9th amino acid is replaced with dimethylated lysine, The peptide sequence represented by SEQ. ID. No 6 is the sequence of alpha-helical peptide represented by SEQ. ID. No 1 in which the 10th amino acid is replaced with dimethylated lysine, The peptide sequence represented by SEQ. ID. No 7 is the sequence of alpha-helical peptide represented by SEQ. ID. No 1 in which the 13th amino acid is replaced with dimethylated lysine, The peptide sequence represented by SEQ. ID. No 8 is the sequence of alpha-helical peptide represented by SEQ. ID. No 1 in which the 15th amino acid is replaced with dimethylated lysine, The peptide sequence represented by SEQ. ID. No 9 is the sequence of alpha-helical peptide represented by SEQ. ID. No 1 in which the 2nd and the 3rd amino acids are replaced with dimethylated lysines, The peptide sequence represented by SEQ. ID. No 10 is the sequence of alpha-helical peptide represented by SEQ. ID. No 1 in which the 2nd and the 6th amino acids are replaced with dimethylated lysines, The peptide sequence represented by SEQ. ID. No 11 is the sequence of alpha-helical peptide represented by SEQ. ID. No 1 in which the 2nd and the 9th amino acids are replaced with dimethylated lysines, The peptide sequence represented by SEQ. ID. No 12 is the sequence of alpha-helical peptide represented by SEQ. ID. No 1 in which the 2nd and the 10th amino acids are replaced with dimethylated lysines, The peptide sequence represented by SEQ. ID. No 13 is the sequence of alpha-helical peptide represented by SEQ. ID. No 1 in which the 2nd and the 13th amino acids are replaced with dimethylated lysines, The peptide sequence represented by SEQ. ID. No 14 is the sequence of alpha-helical peptide represented by SEQ. ID. No 1 in which the 2nd and the 15th amino acids are replaced with dimethylated lysines, The peptide sequence represented by SEQ. ID. No 15 is the sequence of alpha-helical peptide represented by SEQ. ID. No 1 in which the 3rd and the 6th amino acids are replaced with dimethylated lysines, The peptide sequence represented by SEQ. ID. No 16 is the sequence of alpha-helical peptide represented by SEQ. ID. No 1 in which the 3rd and the 9th amino acids are replaced with dimethylated lysines, The peptide sequence represented by SEQ. ID. No 17 is the sequence of alpha-helical peptide represented by SEQ. ID. No 1 in which the 3rd and the 10th amino acids are replaced with dimethylated lysines, The peptide sequence represented by SEQ. ID. No 18 is the sequence of alpha-helical peptide represented by SEQ. ID. No 1 in which the 3rd and the 13th amino acids are replaced with dimethylated lysines, The peptide sequence represented by SEQ. ID. No 19 is the sequence of alpha-helical peptide represented by SEQ. ID. No 1 in which the 3rd and the 15th amino acids are replaced with dimethylated lysines, The peptide sequence represented by SEQ. ID. No 20 is the sequence of alpha-helical peptide represented by SEQ. ID. No 1 in which the 6th and the 9th amino acids are replaced with dimethylated lysines, The peptide sequence represented by SEQ. ID. No 21 is the sequence of alpha-helical peptide represented by SEQ. ID. No 1 in which the 6th and the 10th amino acids are replaced with dimethylated lysines, The peptide sequence represented by SEQ. ID. No 22 is the sequence of alpha-helical peptide represented by SEQ. ID. No 1 in which the 6th and the 13th amino acids are replaced with dimethylated lysines, The peptide sequence represented by SEQ. ID. No 23 is the sequence of alpha-helical peptide represented by SEQ. ID. No 1 in which the 6th and the 15th amino acids are replaced with dimethylated lysines, The peptide sequence represented by SEQ. ID. No 24 is the sequence of alpha-helical peptide represented by SEQ. ID. No 1 in which the 9th and the 10th amino acids are replaced with dimethylated lysines, The peptide sequence represented by SEQ. ID. No 25 is the sequence of alpha-helical peptide represented by SEQ. ID. No 1 in which the 9th and the 13th amino acids are replaced with dimethylated lysines, The peptide sequence represented by SEQ. ID. No 26 is the sequence of alpha-helical peptide represented by SEQ. ID. No 1 in which the 9th and the 15th amino acids are replaced with dimethylated lysines, The peptide sequence represented by SEQ. ID. No 27 is the sequence of alpha-helical peptide represented by SEQ. ID. No 1 in which the 10th and the 13th amino acids are replaced with dimethylated lysines, The peptide sequence represented by SEQ. ID. No 28 is the sequence of alpha-helical peptide represented by SEQ. ID. No 1 in which the 10th and the 15th amino acids are replaced with dimethylated lysines, The peptide sequence represented by SEQ. ID. No 29 is the sequence of alpha-helical peptide represented by SEQ. ID. No 1 in which the 13th and the 15th amino acids are replaced with dimethylated lysines, The peptide sequence represented by SEQ. ID. No 30 is the sequence of alpha-helical peptide represented by SEQ. ID. No 1 in which the 2nd, the 3rd and the 9th amino acids are replaced with dimethylated lysines, The peptide sequence represented by SEQ. ID. No 31 is the sequence of alpha-helical peptide represented by SEQ. ID. No 1 in which the 2nd, the 6th and the 13th amino acids are replaced with dimethylated lysines, The peptide sequence represented by SEQ. ID. No 32 is the sequence of alpha-helical peptide represented by SEQ. ID. No 1 in which the 2nd, the 6th and the 15th amino acids are replaced with dimethylated lysines, The peptide sequence represented by SEQ. ID. No 33 is the sequence of alpha-helical peptide represented by SEQ. ID. No 1 in which the 2nd, the 9th and the 13th amino acids are replaced with dimethylated lysines, The peptide sequence represented by SEQ. ID. No 34 is the sequence of alpha-helical peptide represented by SEQ. ID.

No 1 in which the 2$^{nd}$, the 9$^{th}$ and the 15$^{th}$ amino acids are replaced with dimethylated lysines, The peptide sequence represented by SEQ. ID. No 35 is the sequence of alpha-helical peptide represented by SEQ. ID. No 1 in which the 2$^{nd}$, the 13$^{th}$ and the 15$^{th}$ amino acids are replaced with dimethylated lysines, The peptide sequence represented by SEQ. ID. No 36 is the sequence of alpha-helical peptide represented by SEQ. ID. No 1 in which the 6$^{th}$, the 10$^{th}$ and the 13$^{th}$ amino acids are replaced with dimethylated lysines, The peptide sequence represented by SEQ. ID. No 37 is the sequence of alpha-helical peptide represented by SEQ. ID. No 1 in which the 6$^{th}$, the 10$^{th}$ and the 15$^{th}$ amino acids are replaced with dimethylated lysines, The peptide sequence represented by SEQ. ID. No 38 is the sequence of alpha-helical peptide represented by SEQ. ID. No 1 in which the 6 h, the 13$^{th}$ and the 15$^{th}$ amino acids are replaced with dimethylated lysines, The peptide sequence represented by SEQ. ID. No 39 is the sequence of alpha-helical peptide represented by SEQ. ID. No 1 in which the 9$^{th}$, the 13$^{th}$ and the 15$^{th}$ amino acids are replaced with dimethylated lysines, The peptide sequence represented by SEQ. ID. No 40 is the sequence of alpha-helical peptide represented by SEQ. ID. No 1 in which the 2$^{nd}$, the 6$^{th}$, the 10$^{th}$ and the 13$^{th}$ amino acids are replaced with dimethylated lysines, The peptide sequence represented by SEQ. ID. No 41 is the sequence of alpha-helical peptide represented by SEQ. ID. No 1 in which the 2$^{nd}$, the 10$^{th}$, the 13$^{th}$ and the 15$^{th}$ amino acids are replaced with dimethylated lysines, The peptide sequence represented by SEQ. ID. No 42 is the sequence of alpha-helical peptide represented by SEQ. ID. No 1 in which the 2$^{nd}$, the 6$^{th}$, the 13$^{th}$ and the 15$^{th}$ amino acids are replaced with dimethylated lysines, The peptide sequence represented by SEQ. ID. No 43 is the sequence of alpha-helical peptide represented by SEQ. ID. No 1 in which the 2$^{nd}$, the 6$^{th}$, the 9$^{th}$ and the 15 amino acids are replaced with dimethylated lysines, The peptide sequence represented by SEQ. ID. No 44 is the sequence of alpha-helical peptide represented by SEQ. ID. No 1 in which the 6$^{th}$, the 9$^{th}$, the 13$^{th}$ and the 15$^{th}$ amino acids are replaced with dimethylated lysines, The peptide sequence represented by SEQ. ID. No 45 is the sequence of alpha-helical peptide represented by SEQ. ID. No 1 in which the 2$^{nd}$, the 6$^{th}$, the 9$^{th}$ the 13$^{th}$ and the 15$^{th}$ amino acids are replaced with dimethylated lysines.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A purified RNA binding peptide selected from among amino sequences SEQ ID NOS:1 to 45.

2. An RNA activity inhibitor comprising the peptide of claim 1 as an effective ingredient.

3. A purified Rev Response Element (RRE) RNA binding peptide according to claim 1, selected from among the amino sequence of SEQ ID NOS:1, 3, 7, 16, 18, 25, and 33.

4. An RNA activity inhibitor comprising the peptide of claim 3.

5. The purified Rev Response Element (RRE) RNA binding peptide according to claim 3, wherein the peptide has the amino acid sequence of SEQ ID NO:16.

6. An RNA activity inhibitor comprising the peptide of claim 5.

7. A purified alpha-helical peptide library of synthetic alpha-helical peptides comprising one or more alpha-helical peptide selected from among amino acid sequences SEQ ID NOS:1 to 45.

8. A method of screening for a target RNA specific binding peptide from the library according to claim 7, comprising:
 (i) synthesizing the target RNA;
 (ii) contacting a peptide from the library of claim 1 with the target RNA;
 (iii) calculating binding strength of the target RNA with the peptide by measuring fluorescence anisotropy of the mixture of the peptide, the target RNA and probe molecule with fluorescence spectrophotometer; and
 (iv) selecting the peptide the specifically binds to the target RNA.

9. The method as set forth in claim 8, wherein the probe molecule is CRP (5-carboxytetramethylrhodamine labeled paromomycin).

10. The method according to claim 8, wherein the target RNA is Rev Response Element (RRE).

* * * * *